United States Patent
Karkanias et al.

(10) Patent No.: US 8,005,692 B2
(45) Date of Patent: Aug. 23, 2011

(54) INFORMATION ACCESS TO SELF-DESCRIBING DATA FRAMEWORK

(75) Inventors: Chris Demetrios Karkanias, Sammamish, WA (US); Stephen Edward Hodges, Cambridge (GB)

(73) Assignee: Microsoft Corporation, Redmond, WA (US)

( * ) Notice: Subject to any disclaimer, the term of this patent is extended or adjusted under 35 U.S.C. 154(b) by 946 days.

(21) Appl. No.: 11/678,249

(22) Filed: Feb. 23, 2007

(65) Prior Publication Data

US 2008/0208620 A1    Aug. 28, 2008

(51) Int. Cl.
*G06F 19/00* (2006.01)
(52) U.S. Cl. .......................................... 705/3
(58) Field of Classification Search ............... 705/2, 3, 705/4; 707/104.1, 3; 600/300; 340/573.1
See application file for complete search history.

(56) References Cited

U.S. PATENT DOCUMENTS

| | | | |
|---|---|---|---|
| 6,611,846 B1 * | 8/2003 | Stoodley | 707/104.1 |
| 2002/0109600 A1 * | 8/2002 | Mault et al. | 340/573.1 |
| 2003/0084035 A1 * | 5/2003 | Emerick, III | 707/3 |
| 2003/0187615 A1 | 10/2003 | Epler et al. | |
| 2004/0225200 A1 * | 11/2004 | Edmundson et al. | 600/300 |
| 2006/0085422 A1 | 4/2006 | Moyaux et al. | |

FOREIGN PATENT DOCUMENTS

| KR | 101998025157 A | 7/1998 |
|---|---|---|
| KR | 1020020075846 A | 10/2002 |
| KR | 1020060054977 A | 5/2006 |

OTHER PUBLICATIONS

International Search Report and Written Opinion dated Jul. 25, 2008 for PCT Patent Application No. PCT/US2008/054810; 3 pages.

\* cited by examiner

*Primary Examiner* — Gerald J. O'Connor
*Assistant Examiner* — John A Pauls
(74) *Attorney, Agent, or Firm* — Turocy & Watson, LLP

(57) ABSTRACT

An overall health strategy system that can change consumer behavior by providing an integrated data platform together with individualized third-party services which leverage the data to supply health-related advice, care and products is provided. An interconnected health-related data network can be leveraged in order to proactively (or retroactively) analyze and share data associated to health of a defined population, race, region, age group, etc. Data can be mined in order to identify consistencies, patterns, trends, etc. which can then be used to establish health-related advice, care, warnings, treatments, product suggestions, product research, target advertising or the like.

20 Claims, 11 Drawing Sheets

INFORMATION ACCESS TO SELF-DESCRIBING DATA FRAMEWORK

BACKGROUND

Computers and computer related technology have evolved significantly over the past several decades to the point where vast amounts of computer readable data is being created and stored daily. Digital computers were initially simply very large calculators designed to aid performance of scientific calculations. Only many years later had computers evolved to a point where they were able to execute stored programs. Subsequent rapid emergence of computing power produced personal computers that were able to facilitate document production and printing, bookkeeping as well as business forecasting, among other things. Constant improvement of processing power coupled with significant advances in computer memory and/or storage devices (as well as expediential reduction in cost) have led to persistence and processing of an enormous volume of data, which continues today. For example, data warehouses are now widespread technologies employed to support business decisions over terabytes of data.

Unfortunately, today, data warehouses are maintained separately within relational databases and are most often directed to application specific environments controlled by a variety of application service providers. A relational database refers to a data storage mechanism that employs a relational model in order to interrelate data. These relationships are defined by a set of tuples that all have a common attribute. The tuples are most often represented in a two-dimensional table, or group of tables, organized in rows and columns.

The sheer volume of collected data in databases (e.g., relational databases) made it nearly impossible for a human being alone to perform any meaningful analysis, as was done in the past. This predicament led to the development of data mining and associated tools. Data mining relates to a process of exploring large quantities of data in order to discover meaningful information about the data that is generally in the form of relationships, patterns and rules. In this process, various forms of analysis can be employed to discern such patterns and rules in historical data for a given application or business scenario. Such information can then be stored as an abstract mathematical model of the historical data, referred to as a data-mining model (DMM). After the DMM is created, new data can be examined with respect to the model to determine if the data fits a desired pattern or rule.

Conventionally, data mining is employed upon data in a closed environment, frequently by large corporations, for example, to understand complex business processes. This can be achieved through discovery of relationships or patterns in data relating to past behavior of a business process. Such patterns can be utilized to improve the performance of a process by exploiting favorable and avoiding problematic patterns.

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

The innovation disclosed and claimed herein, in one aspect thereof, comprises an overall health strategy system that can change consumer behavior by providing an integrated data platform together with individualized third-party services which leverage the data to supply health-related advice, care and products. This combination of health-related data and services can prompt a change in mindset and culture related to the health industry.

Generally, the innovation discloses use of an interconnected health-related data network. More particularly, data can be mined from the health-related data network to establish health-related advice, care, warnings, treatments, product suggestions, product research, target advertising or the like. It is to be understood that this health-related network can be viewed analogously to the financial markets where credit risk is maintained by some third party.

Once the data is captured and in the environment, service providers can make available value-added services in view of the interconnected data. As well, service providers can perform proactive health-related services on behalf of the user. For example, based upon an analysis of the interconnected information, health care providers can prescribe therapy, medicines, etc. As well, suppliers can use the data to target consumers based upon the captured data. As a result of capturing safety information, unique associations of services and organizations can be identified. Thus, mining and analysis of the data can enable suppliers to offer products and services to consumers while being able to identify potential risks in view of specific scenarios (e.g., certain amount of therapy they are undergoing).

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

DETAILED DESCRIPTION

Figure 1:
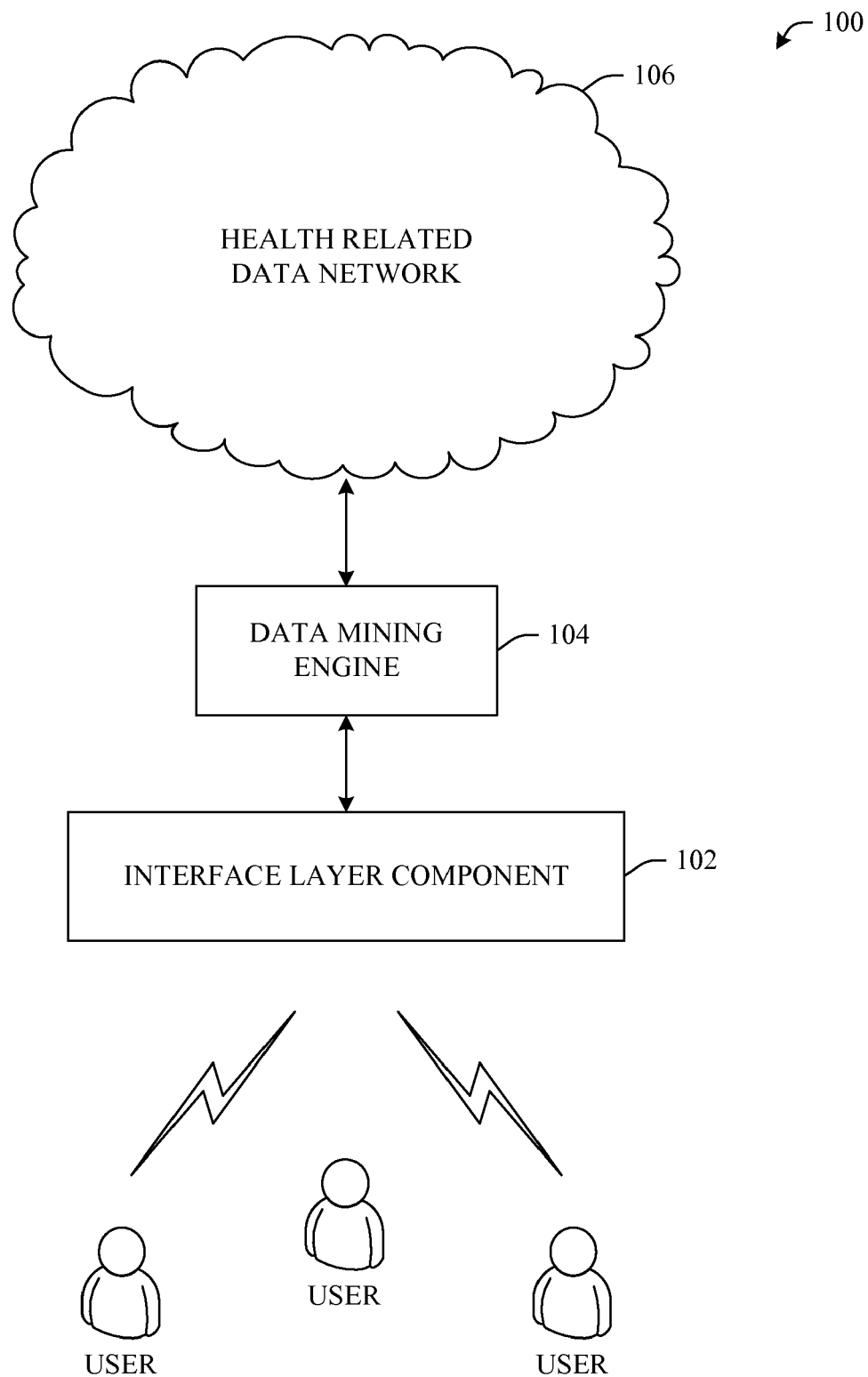
FIG. 1 illustrates a system that leverages a health-related data network in accordance with an aspect of the innovation.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation.

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

As used herein, the term to "infer" or "inference" refer generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources.

Referring initially to the drawings, FIG. 1 illustrates a system 100 that facilitates access to a self-describing data network. In one particular aspect, the system 100 provides for access to and interpretation of health-related data. Generally, system 100 can include an interface layer component 102 that provides a gateway to a data mining engine 104. The data mining engine 104 is capable of extracting specific data and/or identifying patterns and trends associated with data maintained within a health-related data network 106.

More particularly, the data mining component 102 provides a mechanism that can identify implicit, previously unknown, and potentially useful information from the data housed in the communicatively coupled data repository(s) within the health-related data network 106. For example, the data mining component 102 can discern or recognize patterns and/or correlations amongst the stored health-related data. The data mining component 102 can employ a single or combination of analysis techniques including, without limitation, statistics, regression, neural networks, decision trees, Bayesian classifiers, Support Vector Machines, clusters, rule induction, nearest neighbor and the like to locate hidden knowledge within data. In one instance, a data-mining model is built and trained. Subsequently, the trained model can be employed to identify patterns and/or correlations.

Although the aspects described herein are specifically directed to health-related data, alternate aspects of the features, functions and/or benefits of the innovation can be directed to other industry-specific data. By way of example and not limitation, the concepts described herein can be directed to financial information, automobile information, product satisfaction information, media broadcast information, or the like. Thus, alternative aspects which can employ the data manipulation, analysis and sharing concepts described herein are to be considered within the scope of this disclosure and claims appended hereto.

In operation, the interface layer component 102 enables a user to actively and/or intelligently monitor the health-related data network 106 by way of the data mining engine 104. In one particular aspect, data can be actively monitored and mined to identify high as well as low incident events. By way of example, patient data can be automatically captured, e.g., via physiological and/or environmental sensors, and thereafter employed to identify a health-related condition, for example an epidemic.

This health-related condition can be determined or inferred by the data mining engine 104 by heuristically analyzing patterns and trends within data elements of the health-related data network 106. In one specific example, the data elements can be self-describing data elements. This 'self-describing' nature can be enabled by wrapping or embedding each data element with meta-data that describes the element, the source of the element, relationships associated to the element, etc. Effectively, in this aspect, relationships or interconnectivity between the data elements within the health-related data network 106 can be determined or identified through metadata or tags assigned to each of the data elements. Once the interconnectivity is defined, the system 100 can use these associations to evaluate and define trends and/or patterns by way of the data mining engine 104.

Effectively, the health-related data network 106 can be distributed within a cloud or accessible via the Internet. In other aspects, the health-related data network 106 can be distributed throughout multiple locations. For example, data elements within the network 106 can be housed within individual enterprise data storage and accessed therefrom in order to establish interconnectivity between the data elements. Moreover, the distributed self-describing data can be used to identify patterns and trends as they relate to health-related matters (e.g., private drug trials, bioterrorism, epidemics, etc.)

It is to be appreciated that the health-related data network can be structured in such a way that it is effectively an N-dimensional data structure, where N is an integer. In other words, vectors can be drawn between data elements having the same or similar characteristics such that interconnectivity can easily identify to facilitate pattern and trend identification for the purposes of health-related matters. Moreover, the N-dimensional health-related data network can enable the data to be analyzed and/or shared thereby establishing an intelligent system of data sharing as applied to health-related matters. It is to be understood and appreciated that, in aspects, the system 100 of FIG. 1 essentially enables a third party (or group of third parties) to maintain health-related data which can be easily shared and intelligently mined to assess health-related topics.

Figure 2:
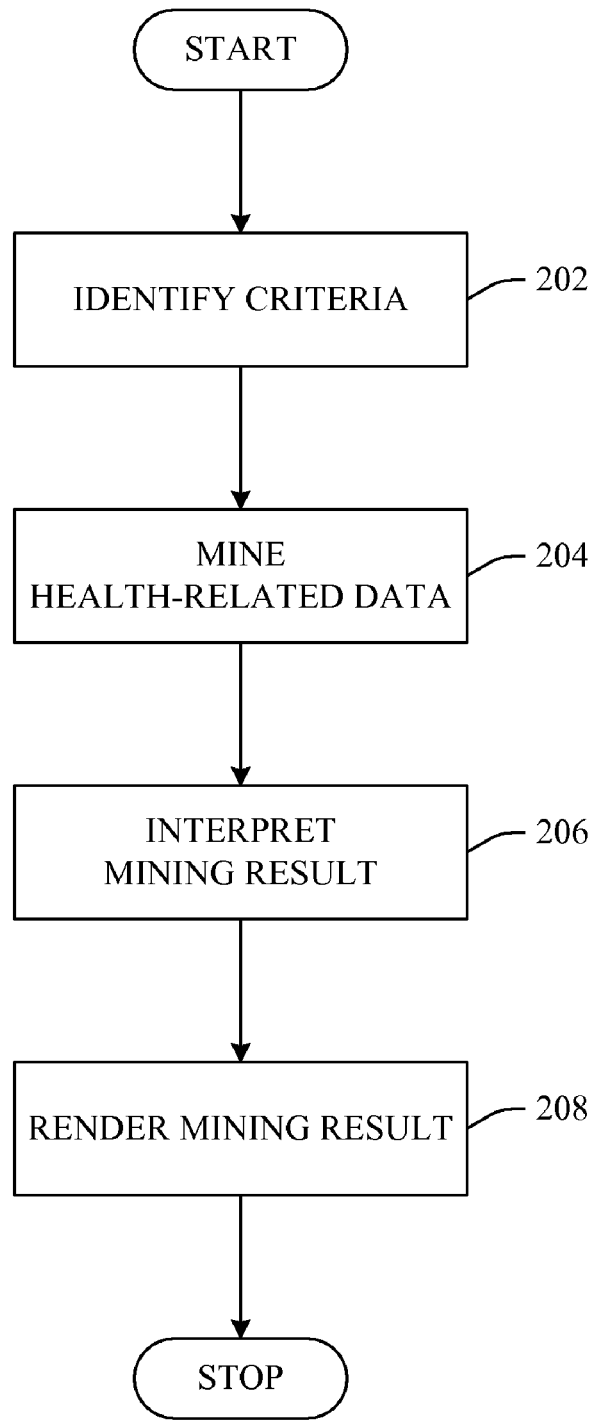
FIG. 2 illustrates an exemplary flow chart of procedures that facilitate analysis and sharing of health-related data in accordance with an aspect of the innovation.

FIG. 2 illustrates a methodology of analyzing and sharing health-related data in accordance with an aspect of the innovation. While, for purposes of simplicity of explanation, the one or more methodologies shown herein, e.g., in the form of a flow chart, are shown and described as a series of acts, it is to be understood and appreciated that the subject innovation is not limited by the order of acts, as some acts may, in accordance with the innovation, occur in a different order and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the innovation.

At 202, criteria by which to monitor and/or share health-related data are identified. For instance, a user can proactively identify (e.g., pre-program) criteria by which to monitor, analyze or share data. As well, the criteria can be inferred, for example, as a function of a monitoring entity context, characteristics of a defined population, notification of a health-related issue, etc.

Once criteria are defined and/or inferred, data can mined from a data pool as related to the criteria. For example, patterns, trends or similarities can be identified within a data pool as a function of the criteria. In an aspect, the data can be self-describing such that metadata and tags can be employed to effectuate mining of the data.

At 206, mining results and/or data sets can be interpreted to identify health-related issues. By way of example, the results can be interpreted or analyzed to identify health-related outbreaks, to locate persons with the same or similar health issues, to proactively identify health-related concerns, to retroactively diagnose and/or analyze health-related concerns, to assess insurance premiums, to assess efficacy of drugs and drug trials, to suggest therapies or drug treatments, etc.

Finally, the result of the analysis can be rendered or shared as appropriate. For instance, the result can be rendered to a user or some application by which the result can be further processed or distributed as desired. Although possible, it is to be understood that it is not necessary for the mining result to be displayed, but rather, the result can be rendered to an application or sub-process for further analysis or storage.

Figure 3:
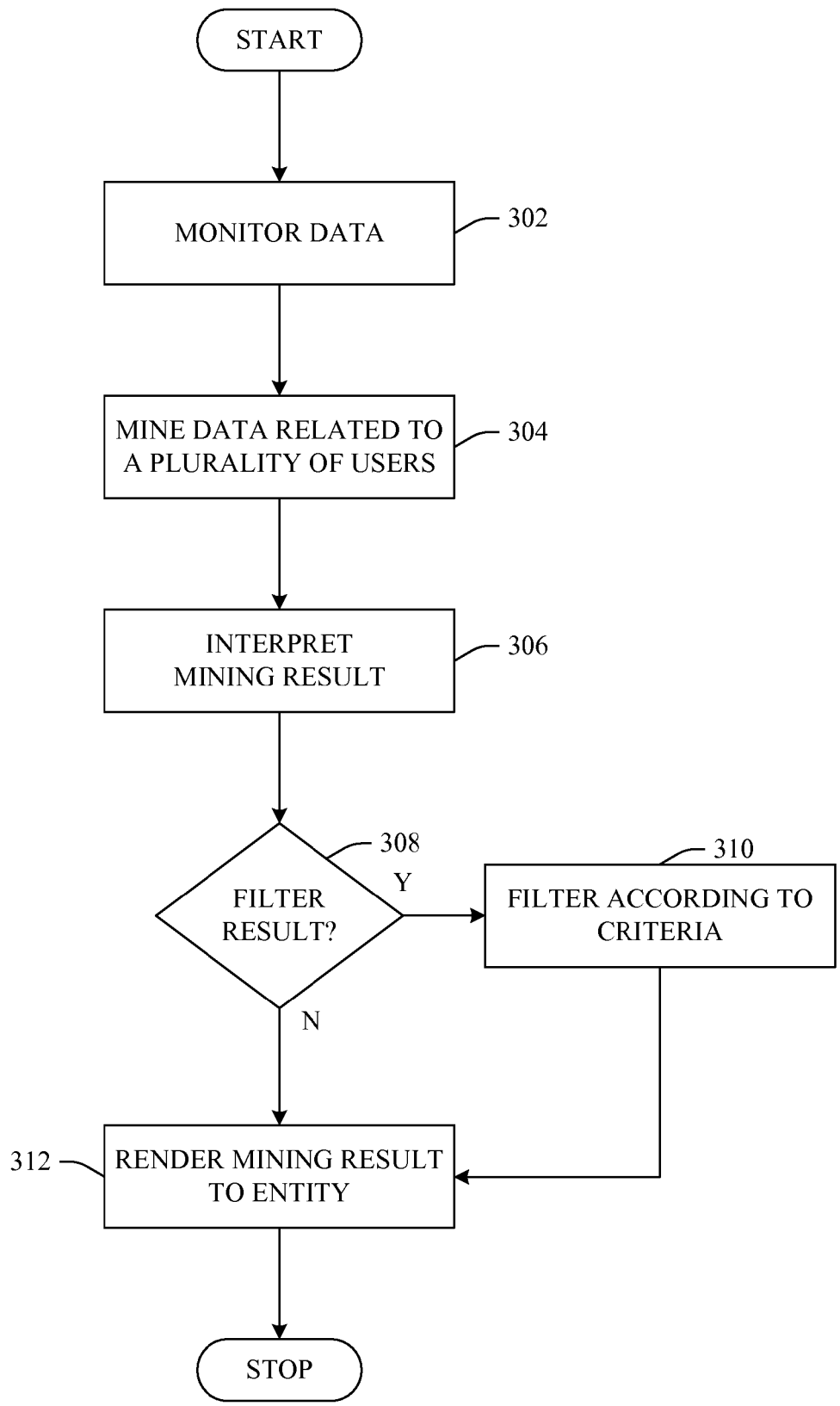
FIG. 3 illustrates an exemplary flow chart of procedures that facilitate mining and rendering health-related data in accordance with an aspect of the innovation.

Referring now to FIG. 3, there is illustrated a methodology of monitoring health-related data in accordance with the innovation. At 302, health-related data can be monitored according to specific and/or distributed locations. For example, data can be monitored with respect to storage within a conventional relational database model. Similarly, cloud based or distributed data models can also be monitored with regard to health-related data.

At 304, data can be mined as associated or applicable to a plurality of users. By way of example, in aspects, the data can be pulled from the storage model and analyzed therefrom in order to extract specific data, identify trends or patterns, etc. Similarly, data can be actively pushed to a data mining engine by which analysis can occur. At 306, the mining result set can be interpreted with regard to a desired goal or preference.

At 308, determination can be made if the result set should be filtered with regard to a defined or inferred criteria, rule, preference, etc. If filtering is desired, at 310, the results can be filtered and rendered at 312. However, if filtering is not desired, the result set can be rendered at 312. By way of example, suppose a specific condition has been diagnosed in adolescents of a defined region. Here, the methodology can be employed to identify individuals having similar criteria and symptoms as those affected by the condition (e.g., temperature, blood pressure, fever, rash, fatigue). However, because the specific condition may only be of concern for adolescents, although adults having the defined criteria and symptoms may be identified, the methodology can automatically filter the results based upon other criteria (e.g., age, race, etc.) in order to provide a more meaningful analysis of the health-related matter.

Figure 4:
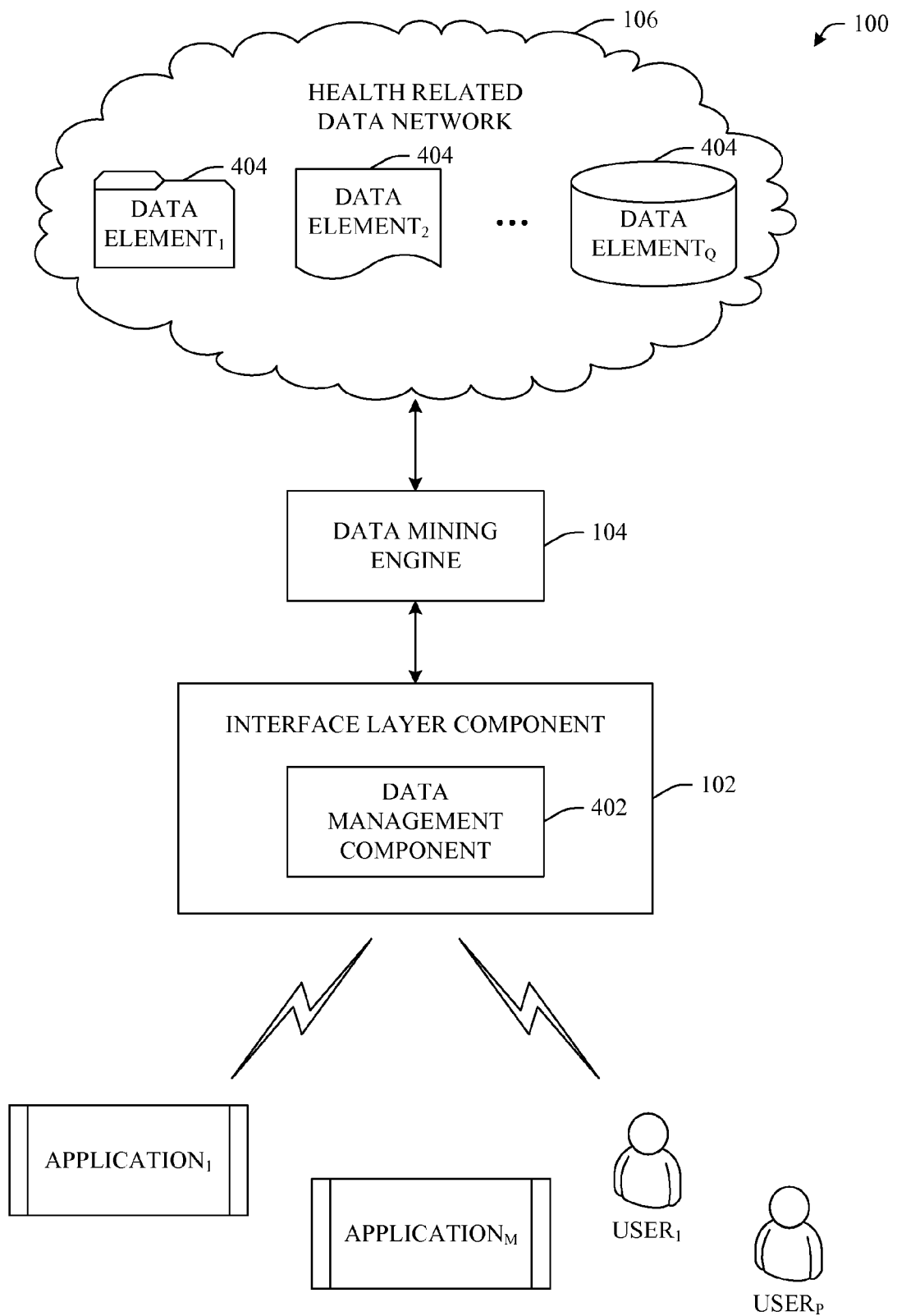
FIG. 4 illustrates a block diagram of an example system that employs a data management component to establish interface between users/applications and a health-related data network.

FIG. 4 illustrates an alternative block diagram of system 100 that facilitates leveraging health-related in accordance with the innovation. More particularly, system 100 of FIG. 4 illustrates a data management component 402 located within the interface layer component 102. This data management component 402 enables both input and output of data to applications and/or users. As shown, the data management component 402 can provide a gateway between 1 to M applications or 1 to P users, where M and P are integers. For example, data can be input into the health-related data network 106 via data management component 402 or rendered from the health-related data network via the data management component 402.

FIG. 4 also illustrates that, as described supra, health-related data network 106 can include 1 to Q data elements where Q is an integer. As shown, it is to be understood that the 1 to Q data elements 404 can be maintained in most any form or structure known in the art. By way of example, and not limitation, the data elements 404 can be organized in conventional folders, documents, data stores or the like. Moreover, the data can be stored in conventional tables, such as relational database tables. In other aspects, the data can be stored and wrapped or embedded with metadata or tags. This metadata or tag information can facilitate comprehensive and intelligent interconnectivity of the health-related data network 106.

Figure 5:
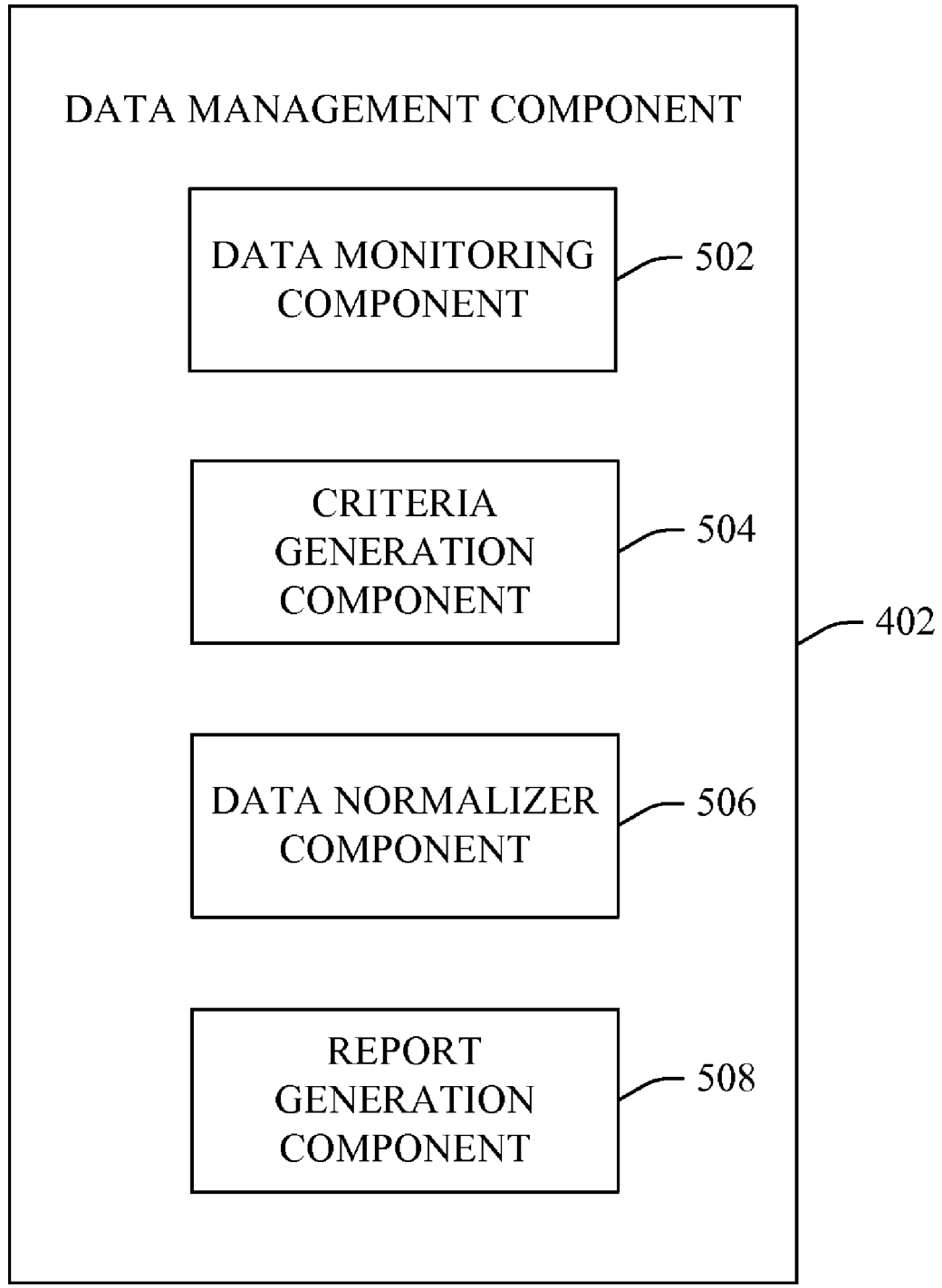
FIG. 5 illustrates a block diagram of an example data management component in accordance with an embodiment.

Referring now to FIG. 5, an example block diagram of a data management component 402 is shown. As illustrated, the data management component 402 can include a data monitoring component 502, a criteria generation component 504, a data normalizer component 506 and/or a report generation component 508. It is to be understood that other aspects of the data management component 402 can include any combination of the components shown in FIG. 5 without departing from the spirit and/or scope of the innovation and claims appended hereto. Each of these components will be described in greater detail below as to how they apply to the functionality of intelligently employing the health-related data network 106 with regard to health-related matters.

Referring first to the data monitoring component 502, this component enables a user or application to actively monitor the health-related data network 106 based upon a predefined, determined or inferred rule or policy in order to intelligently leverage the informational value of health-related data network 106. In a particular example, individuals can potentially be monitored by way of physiological and/or environmental sensors whereby captured information and data can be maintained within the data elements (e.g., 404 of FIG. 4).

In accordance with the data monitoring component 502, data can be monitored in real-time or alternatively in accordance with a predefined or inferred schedule. In operation, the criteria generation component 504 can be employed to establish a policy or rule by which to monitor the data. By way of example, thresholds can be set that automatically identify health-related symptoms in a defined population, region, race, location, etc. Accordingly, the monitoring component 502 can work together with the data mining engine (104 of FIG. 1) to employ the defined thresholds to extract data, identify patterns, trends, etc. In this manner, epidemics can be identified before they are widespread, regional needs for medicines can be established, health care premiums can be more accurately established as a function of region, race, age, etc. Essentially, this data can be leveraged and thereby monetized in ways ranging from, but not limited to, proactive health risk identification, to medicine/treatment advertising, to insurance evaluation, to bioterrorism.

In order to effectively mine the data, it may be necessary to standardize and/or normalize the data into a common format. This normalization is most often required in a relational database scenario. In relational database management, normalization refers to a process that breaks down data into record groups for efficient processing. Once normalized, data can usually be identified by a single key field in the record. For example, patient information is identified by patient number.

The data normalizer component 506 illustrated in FIG. 5 is a mechanism for normalizing or standardizing data formats to optimize mining over such data. While a single format could be forced upon users, the subject innovation can also be flexible enough to allow a plurality of classifications schemes to be employed by users. Accordingly, users may decide to use disparate formats or schemes based on their comfort level or generate their own. Once a user selects a classification, he/she can then tag data accordingly either manually or automatically (e.g., via sensory data capture mechanisms). The data normalizer component 506 can map differing classifications and tags to a standard system so as to simplify the mining process. As a result, the data mining component (e.g., 104 of FIG. 1) need only operate over a single standard format, although it is not limited thereto. Additionally, the normalizer 506 can cleanse data tags and information of typographical, formatting or other errors to facilitate optimized mining.

Figure 6:
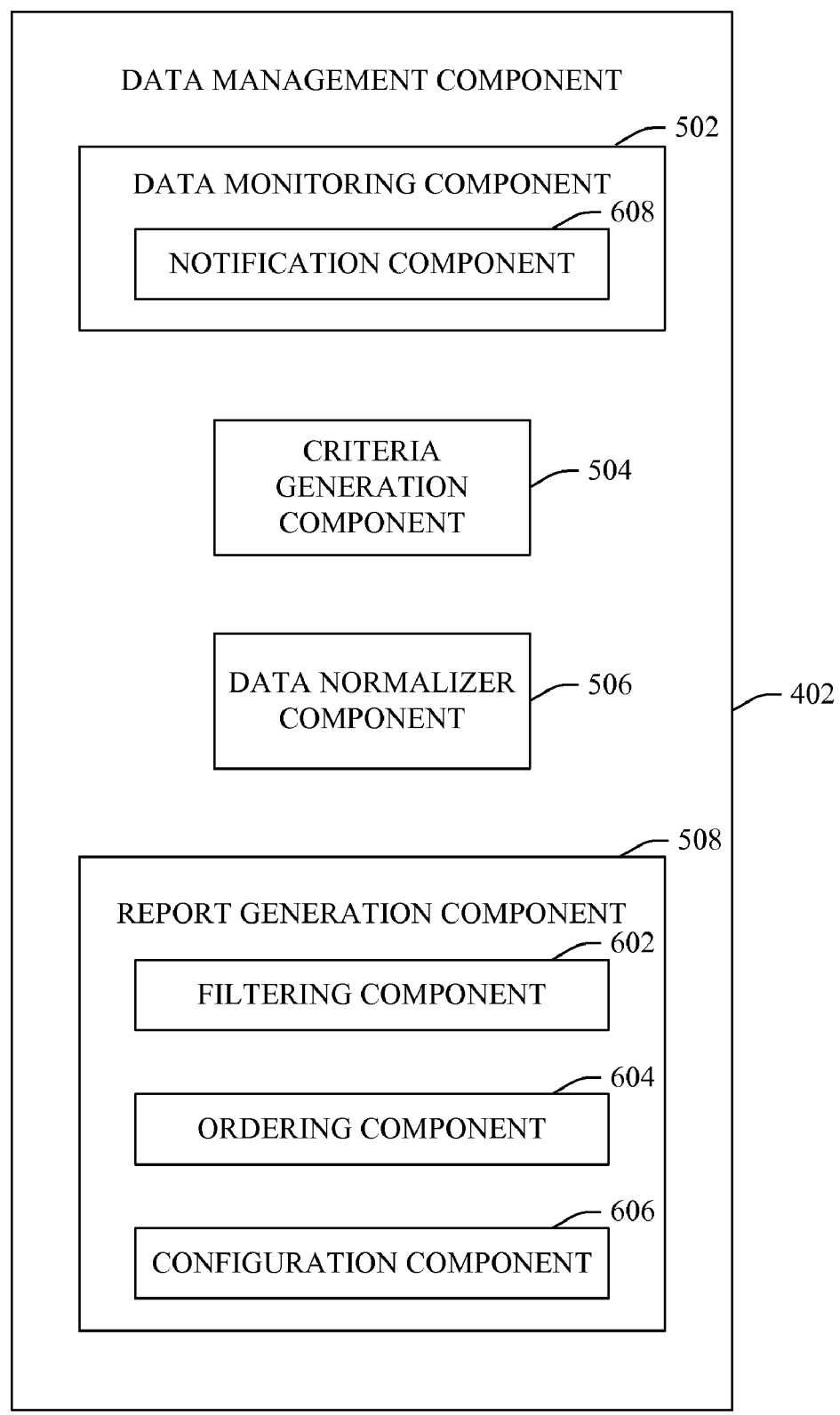
FIG. 6 illustrates an example block diagram of a data management component that enables sharing of health-related data accordance with an aspect.

Once the data is mined and analyzed, the report generation component 508 can facilitate rendering the data in a useful form to a user and/or application. As shown in FIG. 6, the report generation component 508 can include a filtering component 602, an ordering component 604 and/or a configuration component 606. Each of the components can be used to facilitate communication of health-related data to a user.

In operation, the filtering component 602 can be used to limit mined data in accordance with a predefined threshold or policy. Similarly, the ordering component 604 can be employed to order or rank data patterns and/or trends to enhance the informative characteristics of the data. The configuration component 606 can be used to automatically configure the information into a form capable of rendering (e.g., display, printing) via a target device.

With continued reference to FIG. 6, data monitoring component 502 can include a notification component 608 capable of generating and distributing notifications and/or alerts associated to health-related matters. For example, in accordance with a policy, while the data monitoring component 502 can actively monitor patterns, trends, etc. associated with health-related data, the notification component 608 can alert a monitoring entity (e.g., health care professional, insurance provider, homeland security) of any scenario where thresholds are exceeded. In other words, unlike the report generation component 508 that can convey data to a user or application in a desired form for continued analysis, the notification component 608 can be employed to alert of concerning situations or situations of interest thereby enabling or prompting necessary action.

In disparate aspects, the notification can be audible, visual, textual, vibratory, etc. or combinations thereof. Essentially, the notification can provide a monitoring entity notice such that, if necessary, action can be taken in view of a given situation. For example, suppose a number of individuals in a defined region show signs of a bioterrorism attack. Here, the system can be employed to monitor captured health-related data and, if deemed necessary, the notification component 608 can be used to alert appropriate entities such that emergency procedures can be put into action. Although this 'bioterrorism' scenario may seem extreme, it is to be understood that the data management component 502 together with the health-related data network can be used to analyze and/or share information about most any health-related issue.

Figure 7:
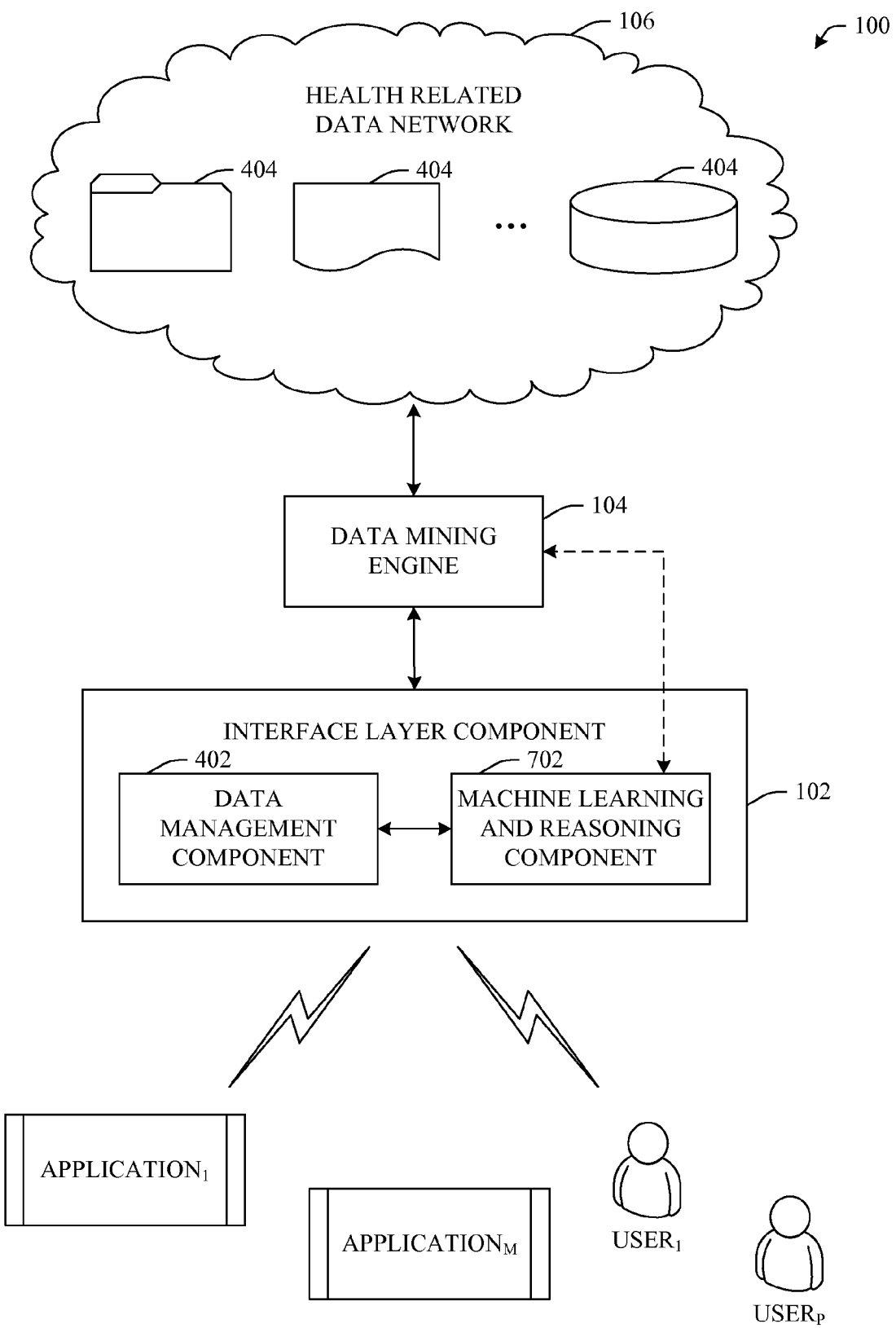
FIG. 7 illustrates an architecture including a machine learning and reasoning (MLR) component that can automate functionality in accordance with an aspect of the innovation.

FIG. 7 illustrates a system 700 that employs a machine learning and reasoning (MLR) component 702 which facilitates automating one or more features in accordance with the subject innovation. The subject innovation (e.g., in connection with data selection, threshold/policy generation) can employ various MLR-based schemes for carrying out various aspects thereof. For example, a process for determining what criteria should be employed in mining, when to monitor, when to alert, how to report, etc. can be facilitated via an automatic classifier system and process. Moreover, where the health-related data network 106 is distributed over various locations, the classifier can be employed to determine which location should be selected in order to effectively evaluate and share data.

A classifier is a function that maps an input attribute vector, $x=(x1, x2, x3, x4, xn)$, to a confidence that the input belongs to a class, that is, $f(x)=confidence(class)$. Such classification can employ a probabilistic and/or statistical-based analysis (e.g., factoring into the analysis utilities and costs) to prognose or infer an action that a user desires to be automatically performed.

A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated from the subject specification, the subject innovation can employ classifiers that are explicitly trained (e.g., via a generic training data) as well as implicitly trained (e.g., via observing user behavior, receiving extrinsic information). For example, SVM's are configured via a learning or training phase within a classifier constructor and feature selection module. Thus, the classifier(s) can be used to automatically learn and perform a number of functions, including but not limited to determining according to a predetermined criteria when to gather data, locations to obtain data, importance of data, when to alert, how to alert, how to render, how to configure, etc.

Figure 8:
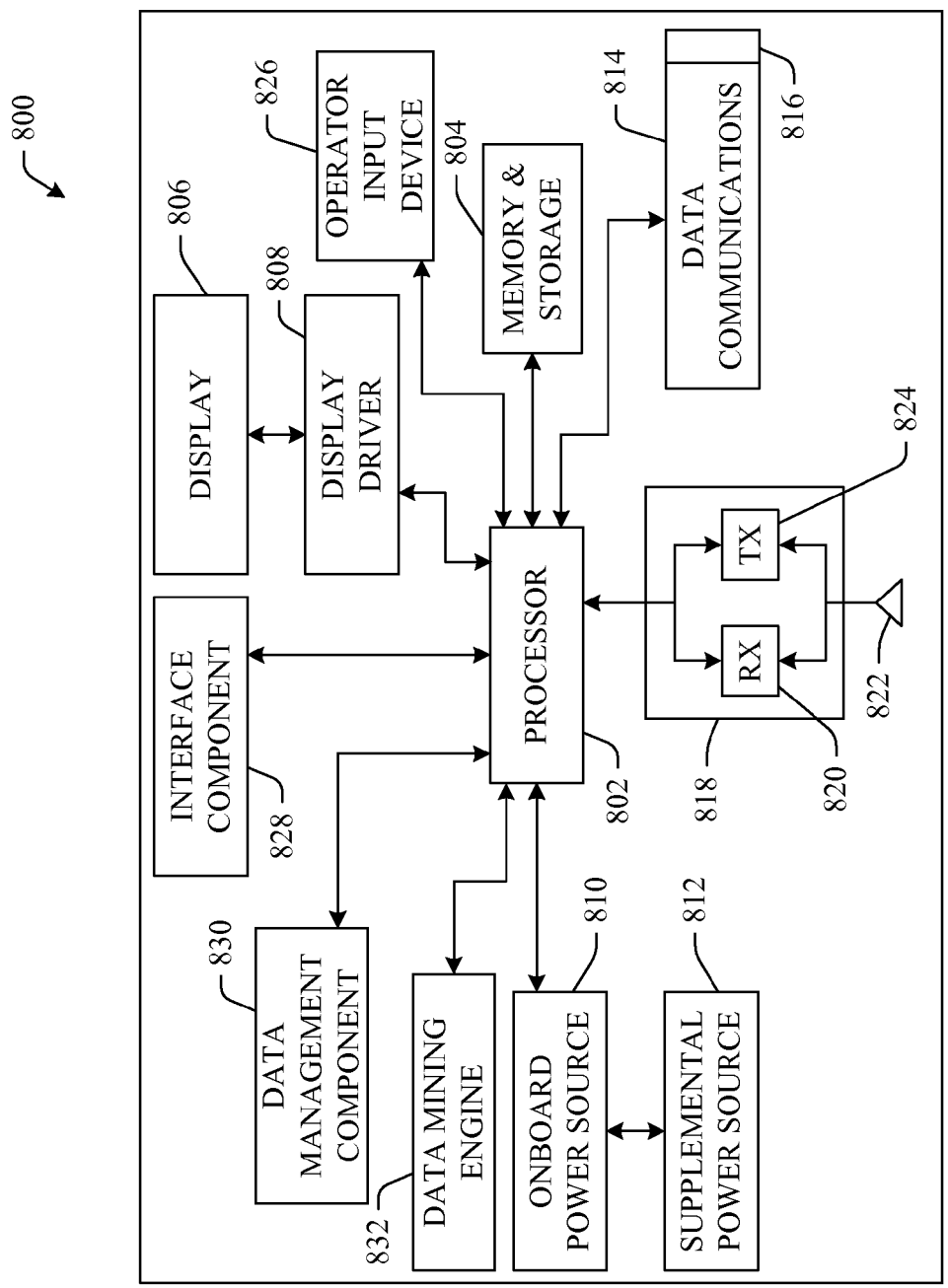
FIG. 8 is a schematic block diagram of a portable handheld device that facilitates analysis and distribution of health-related data according to one aspect of the subject invention.

Referring now to FIG. 8, there is illustrated a schematic block diagram of a portable device 800 according to one aspect of the subject innovation, in which a processor 802 is responsible for controlling the general operation of the device 800. It is to be understood that the portable device 800 can be representative of most any portable device including, but not limited to, a cell phone, smartphone, personal digital assistant (PDA), a personal music player, etc.

The processor 802 can be programmed to control and operate the various components within the device 800 in order to carry out the various functions described herein. The processor 802 can be any of a plurality of suitable processors. The manner in which the processor 802 can be programmed to carry out the functions relating to the subject innovation will be readily apparent to those having ordinary skill in the art based on the description provided herein. As will be described in greater detail infra, an MLR component and/or a rules-based logic component can be used to effect an automatic action of processor 802.

A memory and storage component 804 connected to the processor 802 serves to store program code executed by the processor 802, and also serves as a storage means for storing information such as data, services, metadata, device states or the like. In aspects, this memory and storage component 804 can be employed in conjunction with other memory mechanisms that house health-related data. As well, in other aspects, the memory and storage component 804 can be a stand-alone storage device or otherwise synchronized with a cloud or disparate network based storage means, thereby established a local on-board storage of health-related data.

The memory 804 can be a non-volatile memory suitably adapted to store at least a complete set of the information that is acquired. Thus, the memory 804 can include a RAM or flash memory for high-speed access by the processor 802 and/or a mass storage memory, e.g., a micro drive capable of storing gigabytes of data that comprises text, images, audio, and video content. To this end, it is to be appreciated that the health-related data described herein, e.g., data elements 404 of FIG. 4, can be of most any form including text (e.g., sensor readings), images (e.g., captured image sequences) as well as audio or video content. According to one aspect, the memory 804 has sufficient storage capacity to store multiple sets of information relating to disparate services, and the processor 802 could include a program for alternating or cycling between various sets of information corresponding to disparate services.

A display 806 can be coupled to the processor 802 via a display driver system 808. The display 806 can be a color liquid crystal display (LCD), plasma display, touch screen display or the like. In one example, the display 806 is a touch screen display. The display 806 functions to present data, graphics, or other information content. Additionally, the display 806 can display a variety of functions that control the execution of the device 800. For example, in a touch screen example, the display 806 can display touch selection buttons which can facilitate a user to interface more easily with the functionalities of the device 800.

Power can be provided to the processor 802 and other components forming the hand-held device 800 by an onboard power system 810 (e.g., a battery pack). In the event that the power system 810 fails or becomes disconnected from the device 800, a supplemental power source 812 can be employed to provide power to the processor 802 (and other components (e.g., sensors, image capture device)) and to charge the onboard power system 810. The processor 802 of the device 800 can induce a sleep mode to reduce the current draw upon detection of an anticipated power failure.

The device 800 includes a communication subsystem 814 having a data communication port 816, which is employed to interface the processor 802 with a remote computer, server, service, or the like. The port 816 can include at least one of Universal Serial Bus (USB) and IEEE 1394 serial communications capabilities. Other technologies can also be included, but are not limited to, for example, infrared communication utilizing an infrared data port, Bluetooth™, etc.

The device 800 can also include a radio frequency (RF) transceiver section 818 in operative communication with the processor 802. The RF section 818 includes an RF receiver 820, which receives RF signals from a remote device via an antenna 822 and can demodulate the signal to obtain digital information modulated therein. The RF section 818 also includes an RF transmitter 824 for transmitting information (e.g., data, service) to a remote device, for example, in response to manual user input via a user input 826 (e.g., a keypad) or automatically in response to a detection of entering and/or anticipation of leaving a communication range or other predetermined and programmed criteria.

An interface component 828 can be included that provides a gateway for the device 800 to access a health-related data network. Similarly, a data management component 830 can be provided that facilitate intelligent analysis and sharing of the data in conjunction with a data mining engine 832. It is to be appreciated that these components can enable functionality of like components described supra.

Figure 9:
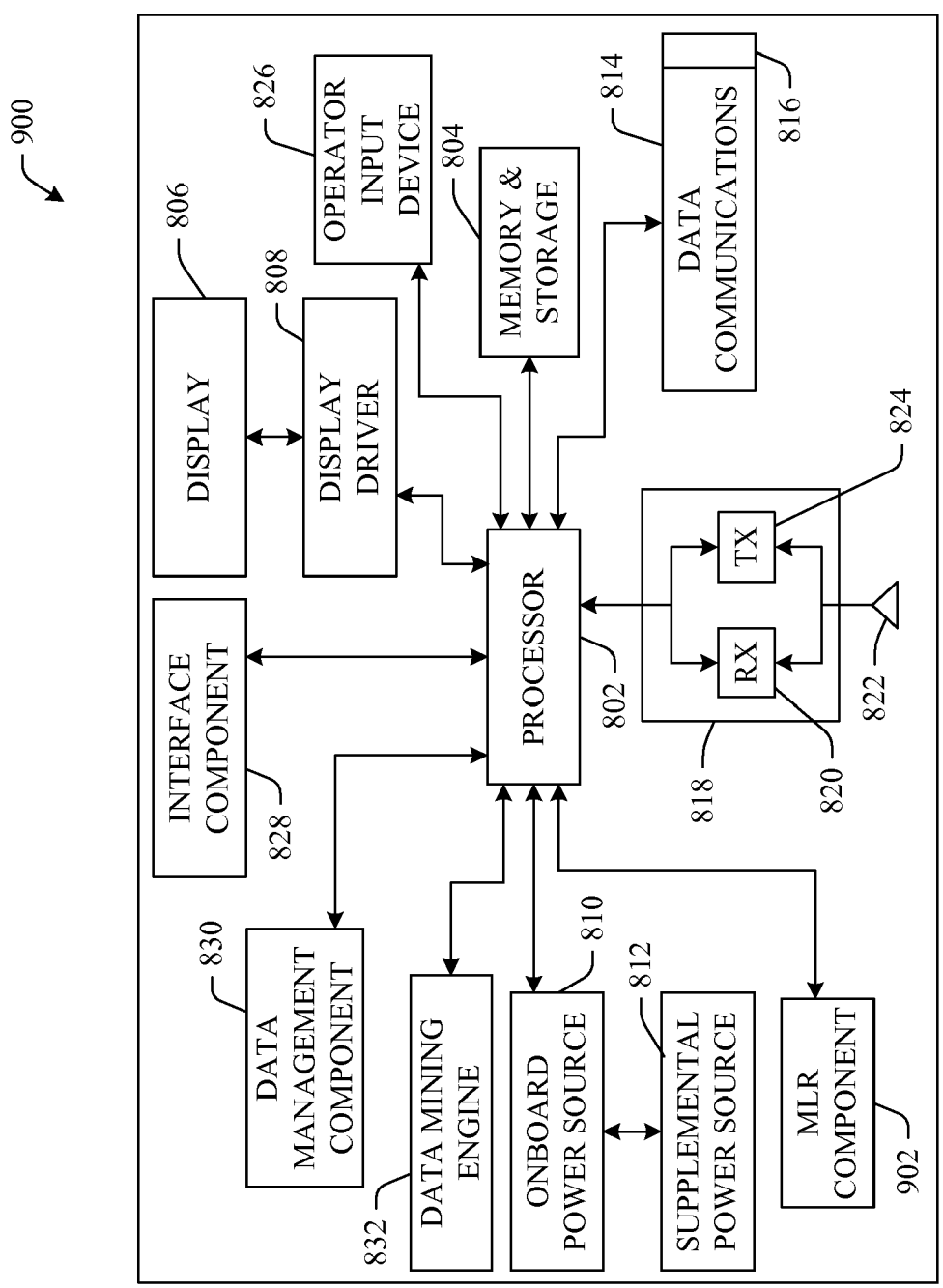
FIG. 9 illustrates an architecture of a portable handheld device including an MLR-based component that can automate functionality in accordance with an aspect of the invention.

FIG. 9 illustrates an example device 900 that employs MLR component 902 which facilitates automating one or more features in accordance with the subject innovation. The subject innovation (e.g., with respect to monitoring, analyzing, sharing, . . . ) can employ various MLR-based schemes for carrying out various aspects thereof. For example, a process for determining when/if to mine data or notify a user of a condition can be facilitated via an automatic classifier system and process. It is to be appreciated that the MLR component 902 illustrated in FIG. 9 can have the same or similar functionality as MLR component 702 of FIG. 7 described in detail supra. It is further to be appreciated that device 900 can be equipped with an optional rules-based component (not shown) that facilitates policies and/or threshold based logic to be employed in making determinations associated with the functionality described herein.

Figure 10:
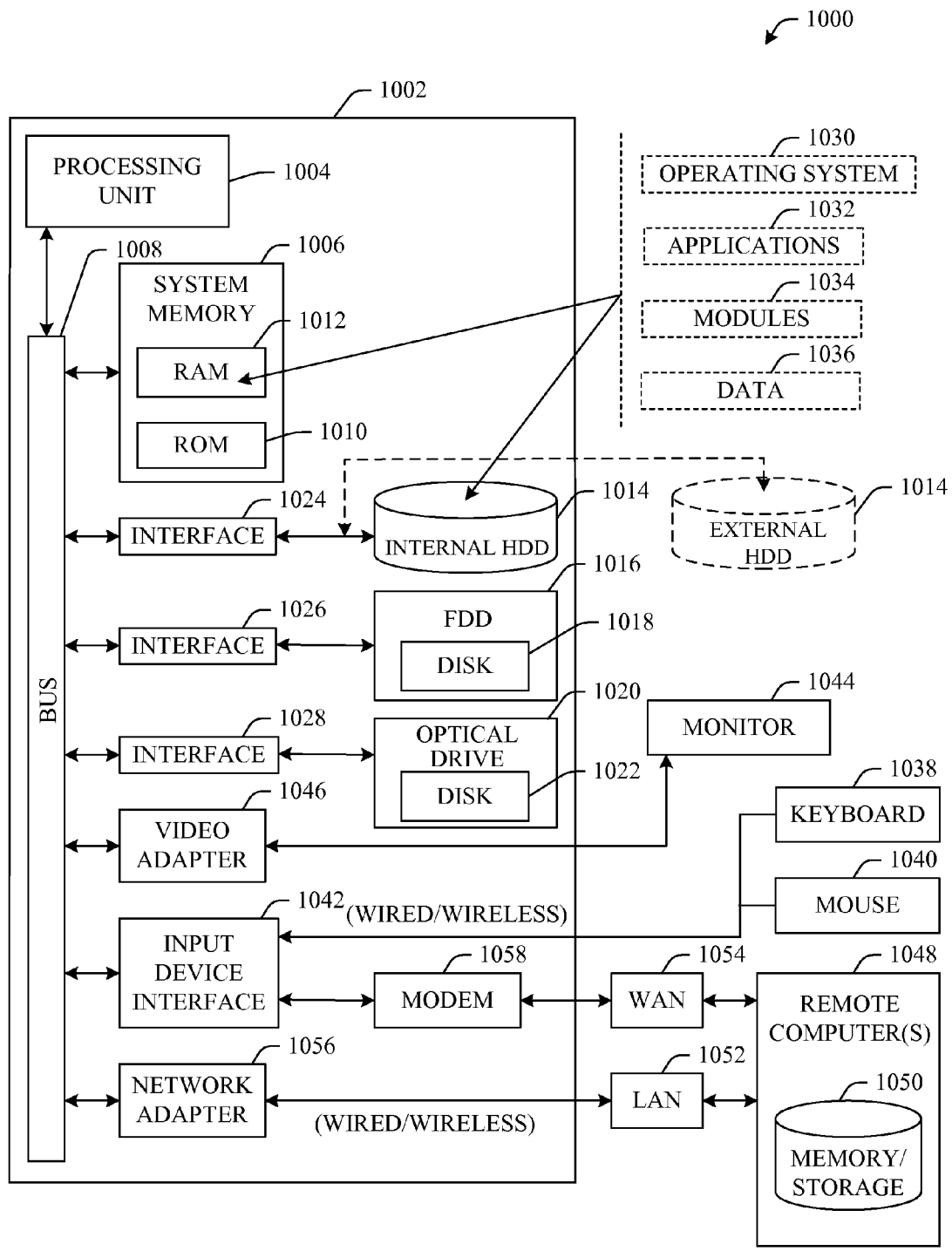
FIG. 10 illustrates a block diagram of a computer operable to execute the disclosed architecture.

Referring now to FIG. 10, there is illustrated a block diagram of a computer operable to execute the disclosed architecture. In order to provide additional context for various aspects of the subject innovation, FIG. 10 and the following discussion are intended to provide a brief, general description of a suitable computing environment 1000 in which the various aspects of the innovation can be implemented. While the innovation has been described above in the general context of computer-executable instructions that may run on one or more computers, those skilled in the art will recognize that the innovation also can be implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

With reference again to FIG. 10, the exemplary environment 1000 for implementing various aspects of the innovation includes a computer 1002, the computer 1002 including a processing unit 1004, a system memory 1006 and a system bus 1008. The system bus 1008 couples system components including, but not limited to, the system memory 1006 to the processing unit 1004. The processing unit 1004 can be any of various commercially available processors. Dual microprocessors and other multi-processor architectures may also be employed as the processing unit 1004.

The system bus 1008 can be any of several types of bus structure that may further interconnect to a memory bus (with or without a memory controller), a peripheral bus, and a local bus using any of a variety of commercially available bus architectures. The system memory 1006 includes read-only memory (ROM) 1010 and random access memory (RAM) 1012. A basic input/output system (BIOS) is stored in a non-volatile memory 1010 such as ROM, EPROM, EEPROM, which BIOS contains the basic routines that help to transfer information between elements within the computer 1002, such as during start-up. The RAM 1012 can also include a high-speed RAM such as static RAM for caching data.

The computer 1002 further includes an internal hard disk drive (HDD) 1014 (e.g., EIDE, SATA), which internal hard disk drive 1014 may also be configured for external use in a suitable chassis (not shown), a magnetic floppy disk drive (FDD) 1016, (e.g., to read from or write to a removable diskette 1018) and an optical disk drive 1020, (e.g., reading a CD-ROM disk 1022 or, to read from or write to other high capacity optical media such as the DVD). The hard disk drive 1014, magnetic disk drive 1016 and optical disk drive 1020 can be connected to the system bus 1008 by a hard disk drive interface 1024, a magnetic disk drive interface 1026 and an optical drive interface 1028, respectively. The interface 1024 for external drive implementations includes at least one or both of Universal Serial Bus (USB) and IEEE 1394 interface technologies. Other external drive connection technologies are within contemplation of the subject innovation.

The drives and their associated computer-readable media provide nonvolatile storage of data, data structures, computer-executable instructions, and so forth. For the computer 1002, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the exemplary operating environment, and further, that any such media may contain computer-executable instructions for performing the methods of the innovation.

A number of program modules can be stored in the drives and RAM 1012, including an operating system 1030, one or more application programs 1032, other program modules 1034 and program data 1036. All or portions of the operating system, applications, modules, and/or data can also be cached in the RAM 1012. It is appreciated that the innovation can be implemented with various commercially available operating systems or combinations of operating systems.

A user can enter commands and information into the computer 1002 through one or more wired/wireless input devices, e.g., a keyboard 1038 and a pointing device, such as a mouse 1040. Other input devices (not shown) may include a microphone, an IR remote control, a joystick, a game pad, a stylus pen, touch screen, or the like. These and other input devices are often connected to the processing unit 1004 through an input device interface 1042 that is coupled to the system bus 1008, but can be connected by other interfaces, such as a parallel port, an IEEE 1394 serial port, a game port, a USB port, an IR interface, etc.

A monitor 1044 or other type of display device is also connected to the system bus 1008 via an interface, such as a video adapter 1046. In addition to the monitor 1044, a computer typically includes other peripheral output devices (not shown), such as speakers, printers, etc.

The computer 1002 may operate in a networked environment using logical connections via wired and/or wireless communications to one or more remote computers, such as a remote computer(s) 1048. The remote computer(s) 1048 can be a workstation, a server computer, a router, a personal computer, portable computer, microprocessor-based entertainment appliance, a peer device or other common network node, and typically includes many or all of the elements described relative to the computer 1002, although, for purposes of brevity, only a memory/storage device 1050 is illustrated. The logical connections depicted include wired/wireless connectivity to a local area network (LAN) 1052 and/or larger networks, e.g., a wide area network (WAN) 1054. Such LAN and WAN networking environments are commonplace in offices and companies, and facilitate enterprise-wide computer networks, such as intranets, all of which may connect to a global communications network, e.g., the Internet.

When used in a LAN networking environment, the computer 1002 is connected to the local network 1052 through a wired and/or wireless communication network interface or adapter 1056. The adapter 1056 may facilitate wired or wireless communication to the LAN 1052, which may also include a wireless access point disposed thereon for communicating with the wireless adapter 1056.

When used in a WAN networking environment, the computer 1002 can include a modem 1058, or is connected to a communications server on the WAN 1054, or has other means for establishing communications over the WAN 1054, such as by way of the Internet. The modem 1058, which can be internal or external and a wired or wireless device, is connected to the system bus 1008 via the serial port interface 1042. In a networked environment, program modules depicted relative to the computer 1002, or portions thereof, can be stored in the remote memory/storage device 1050. It will be appreciated that the network connections shown are exemplary and other means of establishing a communications link between the computers can be used.

The computer 1002 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi and Bluetooth™ wireless technologies. Thus, the communication can be a predefined structure as with a conventional network or simply an ad hoc communication between at least two devices.

Wi-Fi, or Wireless Fidelity, allows connection to the Internet from a couch at home, a bed in a hotel room, or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11(a, b, g, etc.) to provide secure, reliable, fast wireless connectivity. A Wi-Fi network can be used to connect computers to each other, to the Internet, and to wired networks (which use IEEE 802.3 or Ethernet). Wi-Fi networks operate in the unlicensed 2.4 and 5 GHz radio bands, at an 11 Mbps (802.11a) or 54 Mbps (802.11b) data rate, for example, or with products that contain both bands (dual band), so the networks can provide real-world performance similar to the basic 10BaseT wired Ethernet networks used in many offices.

Figure 11:
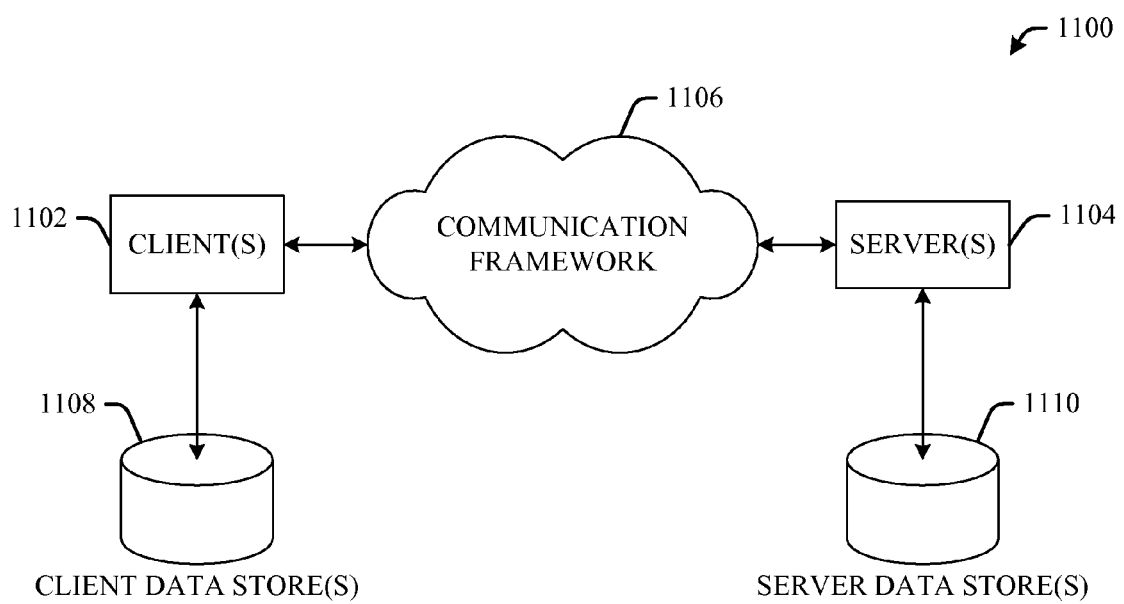
FIG. 11 illustrates a schematic block diagram of an exemplary computing environment in accordance with the subject innovation.

Referring now to FIG. 11, there is illustrated a schematic block diagram of an exemplary computing environment 1100 in accordance with the subject innovation. The system 1100 includes one or more client(s) 1102. The client(s) 1102 can be hardware and/or software (e.g., threads, processes, computing devices). The client(s) 1102 can house cookie(s) and/or associated contextual information by employing the innovation, for example.

The system 1100 also includes one or more server(s) 1104. The server(s) 1104 can also be hardware and/or software (e.g., threads, processes, computing devices). The servers 1104 can house threads to perform transformations by employing the innovation, for example. One possible communication between a client 1102 and a server 1104 can be in the form of a data packet adapted to be transmitted between two or more computer processes. The data packet may include a cookie and/or associated contextual information, for example. The system 1100 includes a communication framework 1106 (e.g., a global communication network such as the Internet) that can be employed to facilitate communications between the client(s) 1102 and the server(s) 1104.

Communications can be facilitated via a wired (including optical fiber) and/or wireless technology. The client(s) 1102 are operatively connected to one or more client data store(s) 1108 that can be employed to store information local to the client(s) 1102 (e.g., cookie(s) and/or associated contextual information). Similarly, the server(s) 1104 are operatively connected to one or more server data store(s) 1110 that can be employed to store information local to the servers 1104.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system comprising at least one processor coupled to at least one machine-readable medium storing instructions executable by the at least one processor to implement:

an interface layer component configured to provide a gateway to a data network, wherein the data network maintains a plurality of health-related data elements each wrapped or embedded with meta-data respectively describing at least the element, a source of the element, and relationships associated to the element, and arranged in an N-dimensional structure, N an integer, including vectors connecting ones of the plurality of health-related data elements having same or similar characteristics;

a data mining engine configured to at least one of analyze or extract a subset of the health-related data elements within the data network, wherein the interface layer component is further configured to facilitate sharing the analyzed or extracted subset of health-related data elements, and the data mining engine is further configured to automatically establish a pattern associated with the subset of health-related data elements, the pattern to prompt one of a public or private action;

a monitoring/analysis component configured to dynamically monitor the data network and prompt the data mining engine upon identification of relevant health-related data based on pre-programmed criteria and criteria inferred as a function of a monitoring entity context, characteristics of a defined population and notification of a health-related issue, the pre-programmed criteria including one of a specific diagnosis, a specific physiological parameter or a specific environmental condition, the prompt to trigger the data mining engine to analyze or extract the subset of health-related data elements based on the pre-programmed and inferred criteria, and a plurality of thresholds associated with health-related symptoms in a defined population, region, race and location, the monitoring/analysis component comprising a plurality of physiological and environmental sensors to capture the relevant health-related data, the monitoring/analysis component further configured to establish proactive health risk identification, and to identify a regional need for medicine and treatment advertising and insurance;

a data normalizer component configured to standardize the plurality of health-related data elements to assist the data mining engine in analysis, at least in part by mapping tags, assigned from a selected classification scheme via sensory data capture mechanisms to the plurality of health-related data elements, to a standard system, and cleansing the tags of errors;

a filtering component configured to limit and render a limited subset of the plurality of health-related data elements, based on a predefined policy; and an ordering component configured to organize the subset of the health-related data elements for display, based on at least one of an order or rank assigned a data pattern or trend.

2. The system of claim 1, further comprising a memory storing multiple sets of information relating to disparate services, and wherein the at least one processor is further configured to execute a program to alternate or cycle between the multiple sets of information corresponding to the disparate services.

3. The system of claim 1, further comprising a data management component configured to share analyzed data with an entity.

4. The system of claim 3, the entity including one of an application or a plug-in.

5. The system of claim 1, wherein the tag errors include at least one of typographical or format errors.

6. The system of claim 1, further comprising a criteria generation component configured to generate criteria for employing by the data mining engine to analyze or extract the subset of the health-related data elements.

7. The system of claim 1, wherein the monitoring/analysis component is further configured to monitor the data network based on a predefined or inferred schedule.

8. The system of claim 1, further comprising a report generation component configured to render one of the subset of health-related data elements or the analysis of the subset of health-related data elements.

9. The system of claim 1, further comprising a notification component configured to provide at least one of an audible, visual, textual or vibratory alert based on monitoring the data network.

10. The system of claim 1, further comprising a configuration component configured to format information of the data network into a form capable of being rendered.

11. The system of claim 1, further comprising a configuration component configured to format the subset of health-related data elements in accordance with a target device.

12. The system of claim 1, further comprising a notification component configured to provide an alert of one of a pattern or trend in the plurality of health-related data elements.

13. The system of claim 1, further comprising a machine learning and reasoning component configured to employ at least one of a probabilistic or a statistical-based analysis to infer an action to be automatically performed.

14. A computer-implemented method of analyzing a health-related data network, comprising:
    capturing a plurality of data elements via physiological and environmental sensors associated with the health-related network;
    pushing the captured plurality of data elements to multiple distributed storage locations;
    dynamically monitoring the plurality of data elements;
    wrapping or embedding each of the plurality of data elements with meta-data respectively describing at least the element, a source of the element, and relationships associated to the element;
    arranging the plurality of data elements in an N-dimensional structure, N an integer, including vectors connecting ones of the plurality of data elements having same or similar characteristics;
    identifying relevant data based on pre-programmed criteria and criteria inferred as a function of a monitoring entity context, characteristics of a defined population and notification of a health-related issue, the pre-programmed criteria including one of a specific diagnosis, a specific physiological parameter or a specific environmental condition,
    establishing a proactive health risk identification, and identifying a regional need for medicine and treatment advertising and insurance;
    based on identifying the relevant data and on a plurality of thresholds associated with health-related symptoms in a defined population, region, race and location, triggering an extraction and analysis of a subset of the plurality of data elements;
    based on the extraction and analysis, automatically establishing a pattern associated with the subset of data elements;
    standardizing the plurality of data elements to assist in the analysis, at least in part by mapping tags, assigned from a selected classification scheme via sensory data capture mechanisms to the plurality of data elements, to a standard system, and cleansing the tags of errors;
    filtering the plurality of data elements to limit and render a limited subset of the plurality of data elements, based on a predefined policy; and
    organizing the subset of the data elements for display, based on at least one of an order or rank assigned a data pattern or trend.

15. The method of claim 14, further comprising analyzing the subset of data elements to identify an event.

16. The method of claim 15, further comprising rendering an identification of the event.

17. The method of claim 14, further comprising establishing a criterion for the dynamically monitoring.

18. The method of claim 14, further comprising:
    identifying a health-related issue based upon the subset of data elements; and
    communicating the health-related issue to an entity.

19. The method of claim 14, further comprising:
    establishing a monitoring criterion;
    identifying a trend related to the health-related data network based upon the criterion;
    analyzing the trend as a function of a defined population; and
    communicating the analysis to an entity.

20. The method of claim 19, further comprising inferring the monitoring criterion based at least in part upon context.

\* \* \* \* \*